(12) United States Patent
Liu et al.

(10) Patent No.: US 9,488,559 B2
(45) Date of Patent: *Nov. 8, 2016

(54) HYDRAULIC AND SPRING COMBINATION DEVICE WITH POSITION-LIMIT SPRING FOR ROCK SAMPLE

(71) Applicant: Sichuan University, Chengdu (CN)

(72) Inventors: Jianfeng Liu, Chengdu (CN); Jianliang Pei, Chengdu (CN); Huining Xu, Chengdu (CN); Lu Wang, Chengdu (CN); Zhiwei Zhou, Chengdu (CN); Yue Zhuo, Chengdu (CN); Feng Dai, Chengdu (CN); Wenxi Fu, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,086

(22) Filed: Feb. 3, 2016

(65) Prior Publication Data
US 2016/0231214 A1   Aug. 11, 2016

(30) Foreign Application Priority Data
Feb. 9, 2015   (CN) .......................... 2015 1 0068200

(51) Int. Cl.
*G01N 3/08*   (2006.01)

(52) U.S. Cl.
CPC ...................... *G01N 3/08* (2013.01)

(58) Field of Classification Search
CPC ............. G01N 3/08; G01N 3/00; G01L 3/24
USPC .................. 73/826, 788, 796, 806, 760, 862
See application file for complete search history.

(56) References Cited

U.S. PATENT DOCUMENTS

| 2008/0276719 A1* | 11/2008 | Xu ........................... G01N 3/08 73/831 |
| 2009/0266548 A1* | 10/2009 | Olsen .................... E21B 49/006 166/308.1 |

* cited by examiner

*Primary Examiner* — Lisa Caputo
*Assistant Examiner* — Nigel Plumb
(74) *Attorney, Agent, or Firm* — Matthias Scholl, PC; Matthias Scholl (57) ABSTRACT

A device for fixing a rock sample, the device including: a lower clamp and an upper clamp. The lower clamp includes: a lower connector connected to a bottom loading base, a lower end cap for fixing samples, a lower chain connecting the lower connector and the lower end cap, a first spiral spring, a first central position-limit mechanism, a second central position-limit mechanism, and a first hydraulic mechanism. The lower end cap includes: a first sample fixing groove and a first connecting segment. The upper clamp includes: an upper connector connected to a top loading base, an upper end cap for fixing the samples, an upper chain connecting with the upper connector and the upper end cap, a second spiral spring, a third central position-limit mechanism, fourth central position-limit mechanism, and a second hydraulic mechanism. The upper end cap includes: a second sample fixing groove and a second connecting segment.

3 Claims, 7 Drawing Sheets

HYDRAULIC AND SPRING COMBINATION DEVICE WITH POSITION-LIMIT SPRING FOR ROCK SAMPLE

CROSS-REFERENCE TO RELATED APPLICATIONS

Pursuant to 35 U.S.C. §119 and the Paris Convention Treaty, this application claims the benefit of Chinese Patent Application No. 201510068200.5 filed Feb. 9, 2015, the contents of which are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a device for conducting direct tensile test on fragile materials, and more particularly to a device for fixing a rock sample.

Description of the Related Art

Direct tensile test is typically adopted for testing tensile strength of rock samples. However, because the fixing device for fixing the rock samples has structural limits, the test results are often inaccurate and the rock samples are easily damaged during the test.

SUMMARY OF THE INVENTION

In view of the above-described problems, it is one objective of the invention to provide a device for fixing a rock sample that ensures the coincidence between the center line of the spiral spring and the center line of the testing machine and the consistence in the loading rigidity at two ends of the test sample and that makes the connection between the chains and the end caps much convenient, thus improving the efficiency.

To achieve the above objective, in accordance with one embodiment of the invention, there is provided a device for fixing a rock sample. The device comprises: a lower clamp and an upper clamp. The lower clamp comprises: a lower connector connected to a bottom loading base of a testing machine, a lower end cap for fixing samples, a lower chain connecting the lower connector and the lower end cap, a first spiral spring, a first central position-limit mechanism, a second central position-limit mechanism, and a first hydraulic mechanism. The lower end cap comprises: a first sample fixing groove and a first connecting segment. The upper clamp comprises: an upper connector connected to a top loading base of the testing machine, an upper end cap for fixing the samples, an upper chain connecting with the upper connector and the upper end cap, a second spiral spring, a third central position-limit mechanism, a fourth central position-limit mechanism, and a second hydraulic mechanism. The upper end cap comprises: a second sample fixing groove and a second connecting segment.

The first central position-limit mechanism, the second central position-limit mechanism, the third central position-limit mechanism, and the fourth central position-limit mechanism have the same structure and each central position-limit mechanism comprises: a position-limit spring assembly, supports, and a connecting plate. Each position-limit spring assembly comprises: a circular support base, three screws, three threaded inserts provided with male threads and female threads, three position-limit springs, and three position-limit bodies. Three screw holes provided with female threads are disposed on a wall of the circular support base. Center lines of the three screw holes all pass through a center of the circular support base. An angle between center lines of neighboring screw holes is 120°. The female threads of the three screw holes match the male threads of the threaded inserts. The female threads of the threaded inserts match male threads of the screws. the position-limit bodies are provided with threaded holes, and female threads of the threaded holes match the male threads of the screws. One ends of the supports are connected to the connecting plate, and the other ends of the supports are connected to the circular support base of the position-limit spring assembly. The three threaded inserts are respectively disposed in the three screw holes of the circular support base. The three screws are assembled with the three threaded inserts respectively. The three position-limit bodies are disposed on the three screws respectively. The three position-limit springs are nested outside the three screws respectively. One ends of the springs contact the position-limit bodies disposed on the screws; and the other ends of the springs contact an internal wall of the circular support base.

The first hydraulic mechanism and the second hydraulic mechanism have the same structure, and each of the first hydraulic mechanism and the second hydraulic mechanism comprises: circular pistons and circular oil cylinders fitting with the circular pistons respectively. The first central position-limit mechanism and the bottom loading base of the testing machine are assembled. The circular support base of the position-limit spring assembly in the first central position-limit mechanism contacts the bottom loading base of the testing machine. The lower connector is disposed in a center hole of the circular support base. One ends of the three screws of the position-limit spring assembly in the first central position-limit mechanism contact an external side of the lower connector respectively. The second central position-limit mechanism and the lower end cap are assembled. The circular support base of the position-limit spring assembly in the second central position-limit mechanism contacts an outer bottom wall of the first sample fixing groove of the lower end cap. The first connecting segment of the lower end cap is disposed in the center hole of the circular support base. One ends of the three screws of the position-limit spring assembly in the second central position-limit mechanism contact an external side of the first connecting segment of the lower end cap. The first hydraulic mechanism and the first central position-limit mechanism are assembled. The circular oil cylinders of the first hydraulic mechanism are connected to the connecting plate of the first central position-limit mechanism. One end of the first spiral spring is connected to the circular pistons of the first hydraulic mechanism, and the other end of the first spiral spring is connected to the connecting plate of the second central position-limit mechanism. The lower chain is disposed in a space enclosed by the first central position-limit mechanism, the first hydraulic mechanism, the first spiral spring, and the second central position-limit mechanism.

The third central position-limit mechanism and the upper end cap are assembled. The circular support base of the position-limit spring assembly in the third central position-limit mechanism contacts an outer bottom wall of the second sample fixing groove of the upper end cap. The second connecting segment of the upper end cap is disposed in the center hole of the circular support base. One ends of the three screws of the position-limit spring assembly in the third central position-limit mechanism respectively contact an external side of the second connecting segment of the upper end cap. The fourth central position-limit mechanism and the top loading base of the testing machine are assembled. The circular support base of the position-limit spring assembly in the fourth central position-limit mechanism contacts the top loading base of the testing machine. The upper connector is disposed in the center hole of the circular support. One ends of the three screws of the position-limit spring assembly in the fourth central position-limit mechanism respectively contact an outer side of the upper connector. The second hydraulic mechanism and the third central position-limit mechanism are assembled. The circular oil cylinders of the second hydraulic mechanism are connected to the connecting plate of the third central position-limit mechanism. One end of the second spiral spring is connected to the circular pistons of the second hydraulic mechanism, and the other end of the second spiral spring is connected to the connecting plate of the fourth central position-limit mechanism. The upper chain is disposed in a space enclosed by the third central position-limit mechanism, the second hydraulic mechanism, the second spiral spring, and the fourth central position-limit mechanism.

In a class of this embodiment, in the first central position-limit mechanism, the second central position-limit mechanism, the third central position-limit mechanism, and the fourth central position-limit mechanism, the supports are four round rods; the connecting plate is a circular plate; the four round rods are uniformly mounted between the circular support base and a circular surface of the connecting plate. Or, the supports are two boards having a circular-arc cross section; the connecting plate is the circular plate; the two boards are symmetrically mounted between the circular support base and the circular surface of the connecting plate.

Advantages of the device for fixing the rock sample according to embodiments of the invention are summarized as follows:

1. Because each of the lower clamp and the upper clamp is provided with the spiral spring and two central position-limit mechanisms, the loading rigidity at both ends of the rock sample during the test are consistent, and the mechanical effect after a peak stress of the rock can be tested more effectively. In addition, the center line of the spiral spring and the center line of the testing machine coincide in the test due to the position-limit spring assembly in the central position-limit mechanisms of the lower clamp and the upper clamp. Thus, the occurrence of additional eccentric force is avoided, and the success rate of the test as well as the accuracy of the test result is improved.

2. Both the upper clamp and the lower clamp are provided with the hydraulic mechanisms. When the chains and the corresponding end caps are connected, the circular pistons drive the spiral springs and the central position-limit mechanisms to move or compress the spiral springs so as to expose the connection part between the chains and the corresponding end caps. The connection between the chains and the end caps are convenient and energy saving, and the test sample is protected from damage before loading, thus improving the efficiency and ensuring the reliability of the test results.

BRIEF DESCRIPTION OF THE DRAWINGS

The invention is described hereinbelow with reference to the accompanying drawings, in which.

In the drawings; the following reference numbers are used: 1. Bottom loading base of a testing machine; 2. Position-limit spring assembly; 2-1. Circular support base; 2-2. Screw; 2-3. Threaded insert; 2-4. Position-limit spring; 2-5. Position-limit body; 3. Lower connector; 4. Support; 5. Connecting plate; 6. Lower chain; 7. Lower bolt; 8. Lower end cap; 9. Rock sample; 10. Upper end cap; 11. Upper bolt; 12. Upper chain; 13. Upper connecter; 14. Top loading base of a testing machine; 15. First spiral spring; and 16. Second spiral spring; 17. Circular piston; 18. Circular oil cylinder; 19. Piston position-limit ring; 20. Sealing washer; 21. Oil pipe; 22. Control valve; 100. First central position-limit mechanism; 200. Second central position-limit mechanism; 300. Third central position-limit mechanism; and 400. Fourth central position-limit mechanism.

DETAILED DESCRIPTION OF THE EMBODIMENTS

For further illustrating the invention, experiments detailing a device for fixing a rock sample in a direct tension test based on position-limit spring assemblies are described below. It should be noted that the following examples are intended to describe and not to limit the invention.

Figure 1:
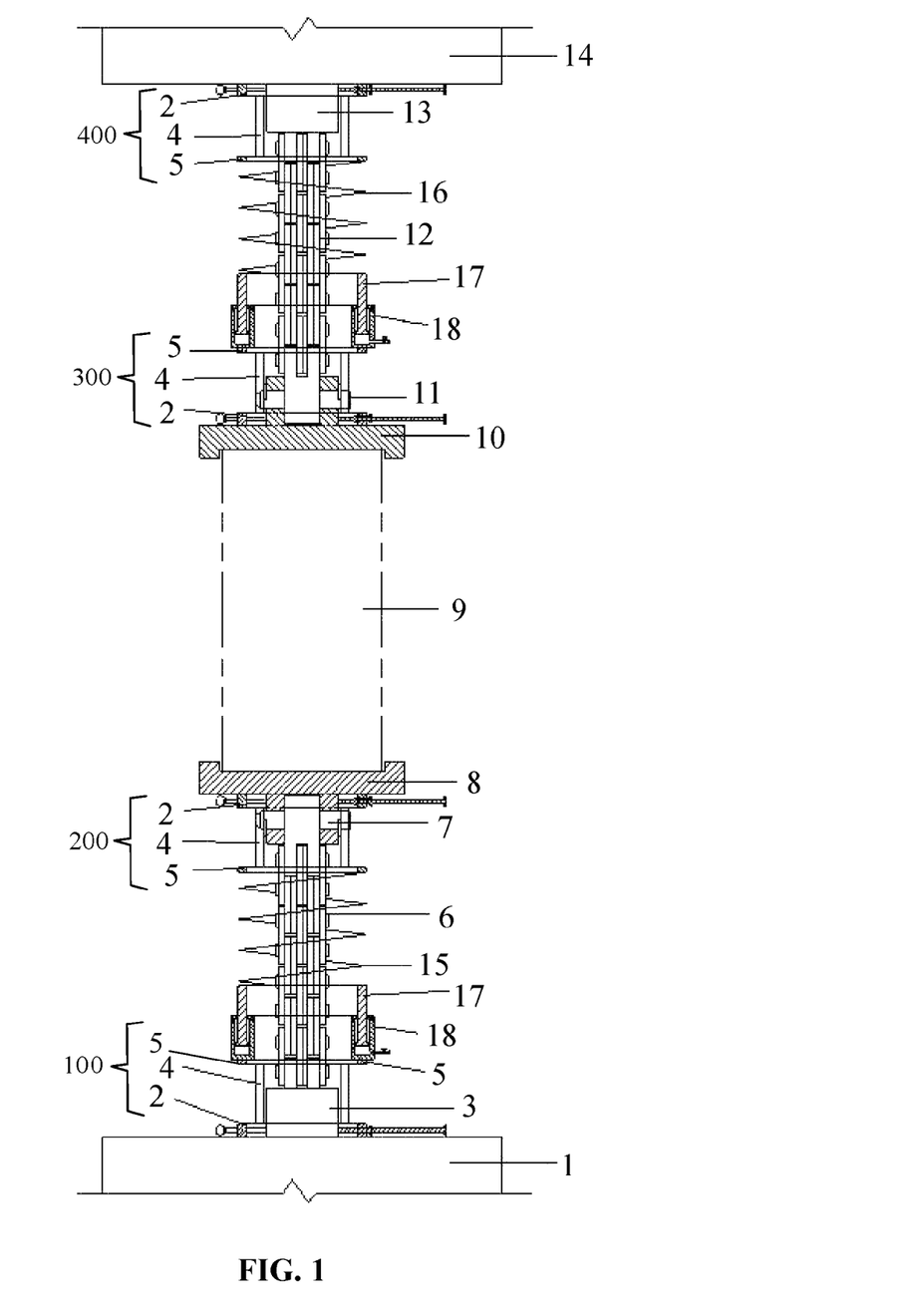
FIG. 1 is a structure diagram of a device for fixing a rock sample in accordance with one embodiment of the invention.

The device for fixing the rock sample comprises: a lower clamp and an upper clamp as shown in the FIG. 1. The lower clamp comprises: a lower connector 3 connected to a bottom loading base 1 of a testing machine, a lower end cap 8 for fixing samples, a lower chain 6 connecting the lower connector and the lower end cap, a first spiral spring 15, a first central position-limit mechanism 100, a second central position-limit mechanism 200, and a first hydraulic mechanism. The lower end cap 8 comprises: a first sample fixing groove and a first connecting segment. The first spiral spring 15 is a cylindrical spiral compression spring. The upper clamp comprises: an upper connector 13 connected to a top loading base 14 of the testing machine, an upper end cap 10 for fixing the samples, an upper chain 12 connecting with the upper connector and the upper end cap, a second spiral spring 16, a third central position-limit mechanism 300, a fourth central position-limit mechanism 400, and a second hydraulic mechanism. The upper end cap 10 comprises: a second sample fixing groove and a second connecting segment. The second spiral spring 16 is the cylindrical spiral compression spring.

Figure 2:
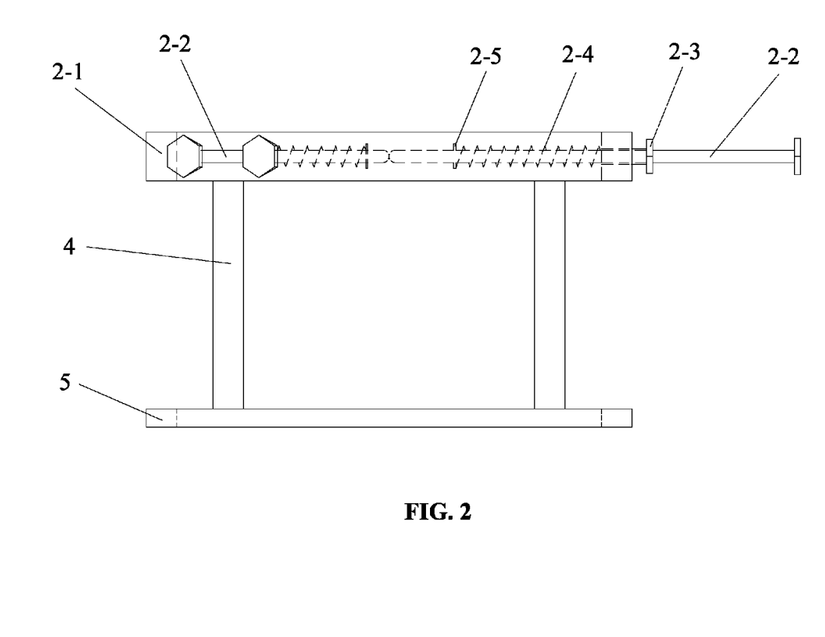
FIG. 2 is a structure diagram of a first central position-limit mechanism, a second central position-limit mechanism, a third central position-limit mechanism, or a fourth central position-limit mechanism in a device for fixing a rock sample (the supports are round rods) in accordance with one embodiment of the invention, and the central position-limit mechanism is in a non-operating state.
Figure 3:
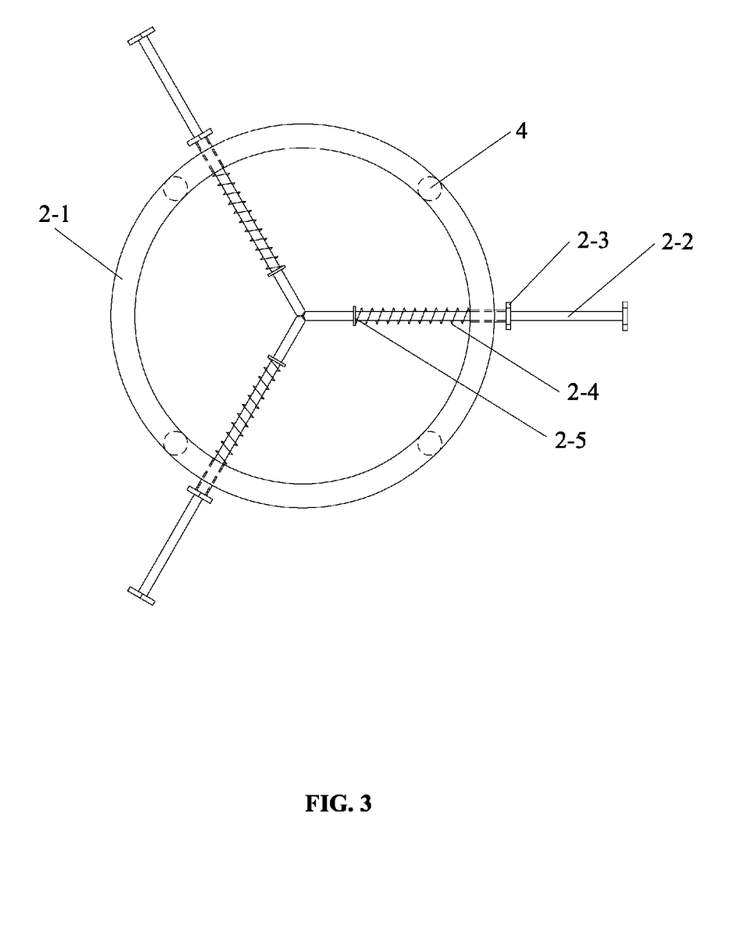
FIG. 3 is a top view of the FIG. 2.

The first central position-limit mechanism 100, the second central position-limit mechanism 200, the third central position-limit mechanism 300, and the fourth central position-limit mechanism 400 have the same structure and each central position-limit mechanism comprises: a position-limit spring assembly 2, supports 4, and a connecting plate 5, as shown in FIGS. 2 and 3. Each position-limit spring assembly 2 comprises: a circular support base 2-1, three screws 2-2, three threaded inserts 2-3 provided with male threads and female threads, three position-limit springs 2-4, and three position-limit bodies 2-5. Three screw holes provided with female threads are disposed on a wall of the circular support base. Center lines of the three screw holes all pass through a center of the circular support base. An angle between the center lines of neighboring screw holes is 120°. The female threads of the three screw holes match the male threads of the threaded inserts 2-3. The female threads of the threaded inserts 2-3 match male threads of the screws 2-2. The position-limit bodies 2-5 are nuts matching the male threads of the screws 2-2. The position-limit springs 2-4 are cylindrical spiral compression springs. The supports 4 are four round rods. The connecting plate 5 is a circular plate, whose outer diameter and inner diameter are identical with an outer diameter an inner diameter of the circular support base 2-1. The four round rods are uniformly mounted between the circular support base 2-1 and a circular surface of the connecting plate 5. One ends of the round rods are connected to the connecting plate 5, and the other ends of the round rods are connected to the circular support base 2-1 of the position-limit spring assembly. The three threaded inserts 2-3 are respectively disposed in the three screw holes of the circular support base. The three screws 2-2 are assembled with the three threaded inserts respectively. The three position-limit bodies 2-5 are disposed on the three screws respectively. The three position-limit springs 2-4 are nested outside the three screws respectively; one ends of the springs contact the position-limit bodies 2-5 disposed on the screws; and the other ends of the springs contact an internal wall of the circular support base 2-1.

Figure 6:
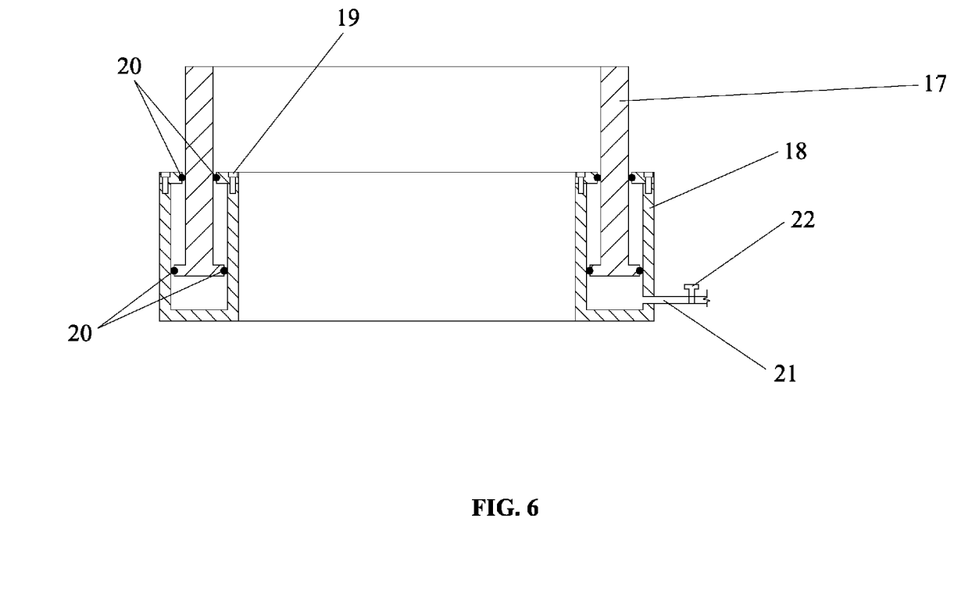
FIG. 6 is a structure diagram of a first hydraulic mechanism or a second hydraulic mechanism in accordance with one embodiment of the invention.
Figure 7:
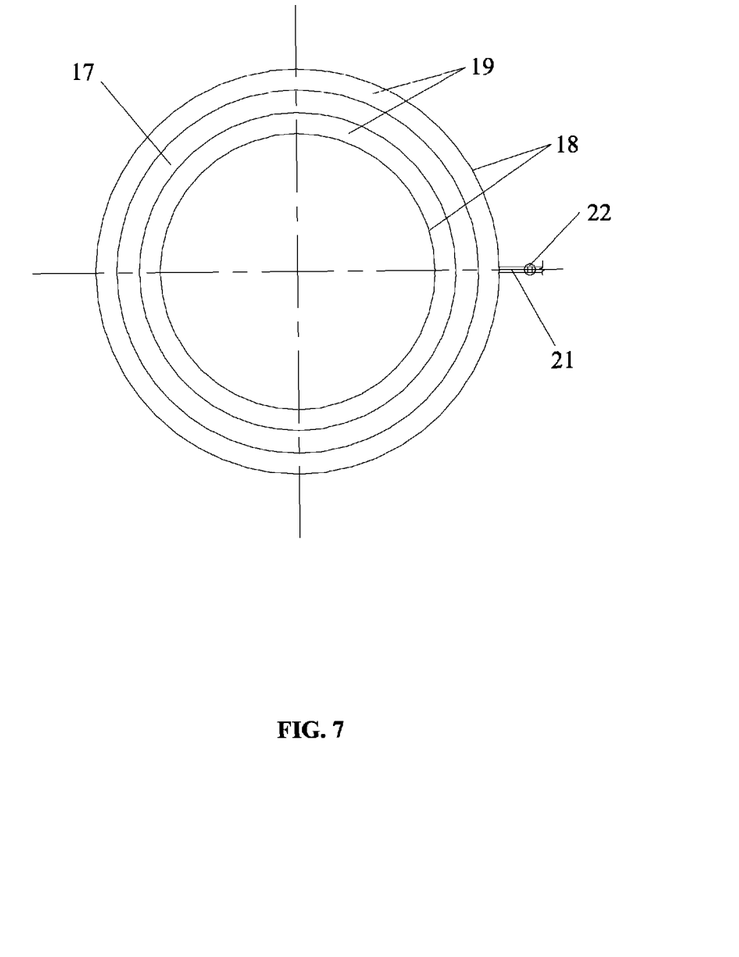
FIG. 7 is a top view of FIG. 6.

As shown in FIGS. 6 and 7, each of the first hydraulic mechanism and the second hydraulic mechanism comprises: circular pistons 17, circular oil cylinders 18, piston position-limit rings 19, and sealing washers 20. One end of each of the circular piston 17 is inserted into a circular cavity of each circular oil cylinder 18. A closed end of the circular cavity of each circular oil cylinder 18 is provided with the oil pipe 21 communicating the circular cavity thereof. The control valve 22 is disposed on each oil pipe 21. Each piston position-limit ring 19 is disposed on an open end of the circular cavity of each circular oil cylinder 18. The sealing washers 20 are disposed on one end of each circular piston 17 inserted into the circular cavity and each piston position-limit ring 19, respectively.

Members or components of the lower clamp are assembled as follows: the first central position-limit mechanism 100 and the bottom loading base 1 of the testing machine are assembled. The circular support base of the position-limit spring assembly in the first central position-limit mechanism 100 contacts the bottom loading base 1 of the testing machine. The lower connector 3 is disposed in a center hole of the circular support base. One ends of the three screws of the position-limit spring assembly in the first central position-limit mechanism 100 contact an external side of the lower connector 3 respectively. The second central position-limit mechanism 200 and the lower end cap 8 are assembled. The circular support base of the position-limit spring assembly in the second central position-limit mechanism 200 contacts an outer bottom wall of the first sample fixing groove of the lower end cap 8. The first connecting segment of the lower end cap 8 is disposed in the center hole of the circular support base. One ends of the three screws of the position-limit spring assembly in the second central position-limit mechanism 200 contact an external side of the first connecting segment of the lower end cap. The first hydraulic mechanism and the first central position-limit mechanism 100 are assembled. The circular oil cylinders 18 of the first hydraulic mechanism are connected to the connecting plate 5 of the first central position-limit mechanism 100. One end of the first spiral spring 15 is connected to the circular pistons 17 of the first hydraulic mechanism, and the other end of the first spiral spring 15 is connected to the connecting plate 5 of the second central position-limit mechanism 200. A lower end of the lower chain 6 is connected to the lower connector 3 disposed on the bottom loading base 1 of the testing machine; and a dismountable connection between the upper end of the lower chain and the lower end cap is formed by a lower bolt 7. The lower chain 6 is disposed in a space enclosed by the first central position-limit mechanism 100, the first hydraulic mechanism, the first spiral spring 15, and the second central position-limit mechanism 200.

Members or components of the upper clamp are assembled as follows: the third central position-limit mechanism 300 and the upper end cap 10 are assembled. The circular support base of the position-limit spring assembly in the third central position-limit mechanism 300 contacts an outer bottom wall of the second sample fixing groove of the upper end cap 10. The second connecting segment of the upper end cap 10 is disposed in the center hole of the circular support base. One ends of the three screws of the position-limit spring assembly in the third central position-limit mechanism 300 respectively contact an external side of the second connecting segment of the upper end cap. The fourth central position-limit mechanism 400 and the top loading base 14 of the testing machine are assembled. The circular support base of the position-limit spring assembly in the fourth central position-limit mechanism 400 contacts the top loading base 14 of the testing machine. The upper connector 13 is disposed in the center hole of the circular support. One ends of the three screws of the position-limit spring assembly in the fourth central position-limit mechanism 400 respectively contact an outer side of the upper connector 13. The second hydraulic mechanism and the third central position-limit mechanism 300 are assembled. The circular oil cylinders 18 of the second hydraulic mechanism are connected to the connecting plate 5 of the third central position-limit mechanism 300. One end of the second spiral spring 16 is connected to the circular pistons 17 of the second hydraulic mechanism, and the other end of the second spiral spring 16 is connected to the connecting plate 5 of the fourth central position-limit mechanism 400. An upper end of the upper chain 12 is connected to the upper connector 13 disposed on the top loading base 14 of the testing machine; and a dismountable connection between the lower end of the upper chain and the upper end cap is formed by an upper bolt 11. The upper chain 12 is disposed in a space enclosed by the third central position-limit mechanism 300, the second hydraulic mechanism, the second spiral spring 16, and the fourth central position-limit mechanism 400.

The mode for mounting the rock sample 9 is shown in the FIG. 1. Both ends of the rock sample are adhered with the first sample fixing groove of the lower end cap 8 and the second sample fixing groove of the upper end cap 10 by a high-strength adhesive.

It should be noted that the installation of the screws 2-2, the threaded inserts 2-3, the position-limit springs 2-4, and the position-limit bodies 2-5 in the position-limit spring assembly 2 are as follows: the three threaded inserts 2-3 and the three screws 2-2 are first assembled; then the three screws 2-2 are inserted into the three screw holes of the circular support base 2-1 respectively; the three position-limit spring 2-4 are respectively sleeved on the segments of the three screws in the center hole of the circular support base; the three position-limit bodies 2-5 are respectively disposed on the segments of the three screws in the center hole of the circular support base. The three position-limit bodies are adjusted to make the three position-limit bodies disposed on positions of the segments in the center hole of the circular support base equidistant from ends thereof. The three position-limit springs are in the same compression state. And then the three screws are disposed on the circular support base by three threaded inserts.

Figure 4:
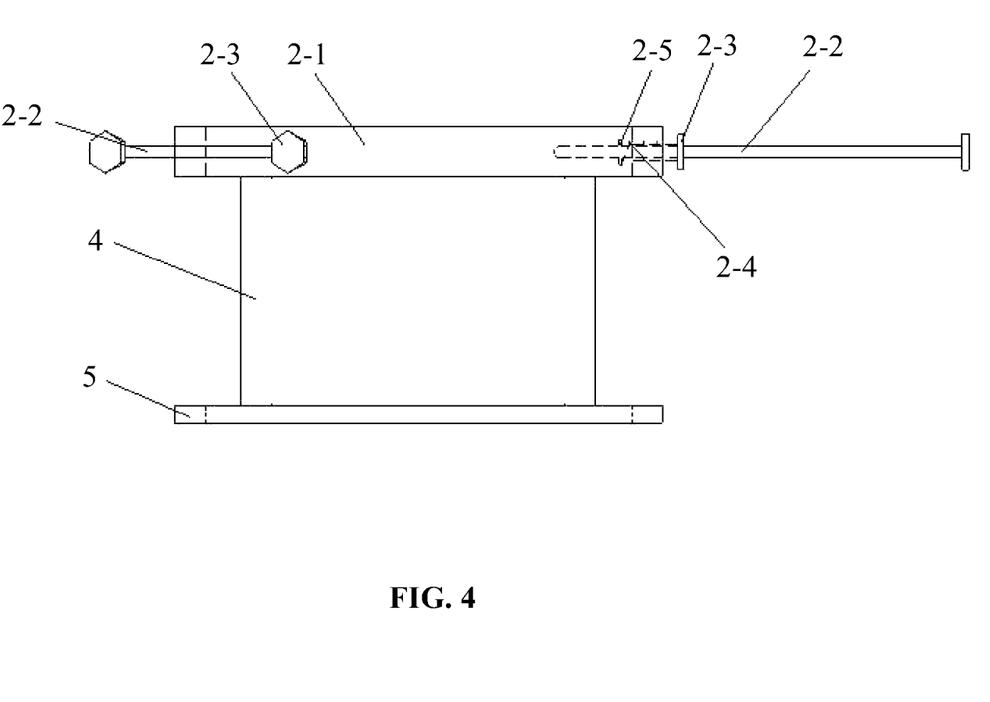
FIG. 4 is a structure diagram of a first central position-limit mechanism, a second central position-limit mechanism, a third central position-limit mechanism, or a fourth central position-limit mechanism in a device for fixing a rock sample (the supports are boards having a circular-arc cross section) in accordance with one embodiment of the invention, and the central position-limit mechanism is in an operating state.
Figure 5:
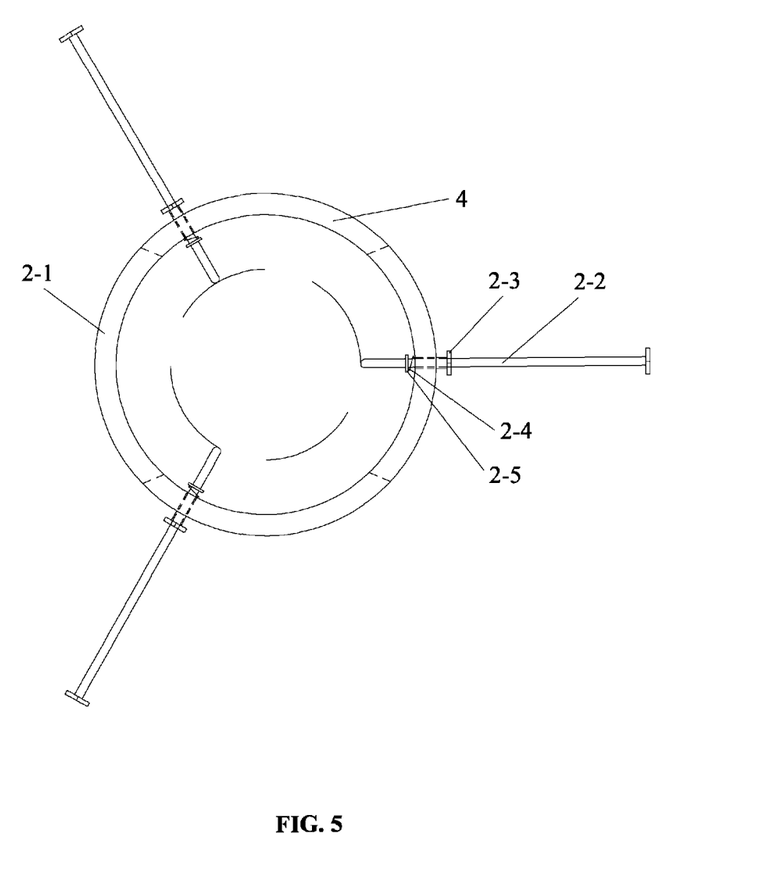
FIG. 5 is a top view of the FIG. 4.

The invention is not limited to the above embodiments. For example, the first central position-limit mechanism 100, the second central position-limit mechanism 200, the third central position-limit mechanism 300, and the fourth central position-limit mechanism 400 can also have the structure shown in FIGS. 4 and 5. That is, the supports 4 are two boards having a circular-arc cross section; the connecting plate 5 is the circular plate; the two boards are symmetrically mounted between the circular support base 2-1 and the circular surface of the connecting plate 5. One ends of the two supports are connected to the connecting plate 5, and the other ends of the two supports are connected to the circular support base 2-1 in the position-limit spring assembly.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for fixing a rock sample, the device comprising:
   a) a lower clamp, the lower clamp comprising: a lower connector connected to a bottom loading base of a testing machine, a lower end cap for fixing samples, a lower chain connecting the lower connector and the lower end cap, a first spiral spring, a first central position-limit mechanism, a second central position-limit mechanism, and a first hydraulic mechanism; the lower end cap comprising: a first sample fixing groove and a first connecting segment;
   b) an upper clamp, the upper clamp comprising: an upper connector connected to a top loading base of the testing machine, an upper end cap for fixing the samples, an upper chain connecting with the upper connector and the upper end cap, a second spiral spring, a third central position-limit mechanism, a fourth central position-limit mechanism, and a second hydraulic mechanism; the upper end cap comprising: a second sample fixing groove and a second connecting segment;
   wherein
   the first central position-limit mechanism, the second central position-limit mechanism, the third central position-limit mechanism, and the fourth central position-limit mechanism have the same structure and each central position-limit mechanism comprises: a position-limit spring assembly, supports, and a connecting plate; each position-limit spring assembly comprises: a circular support base, three screws, three threaded inserts provided with male threads and female threads, three position-limit springs, and three position-limit bodies; three screw holes provided with female threads are disposed on a wall of the circular support base; center lines of the three screw holes all pass through a center of the circular support base; an angle between the center lines of neighboring screw holes is 120°; the female threads of the three screw holes match the male threads of the threaded inserts; the female threads of the threaded inserts match male threads of the screws; the position-limit bodies are provided with threaded holes, and female threads of the threaded holes match the male threads of the screws; one ends of the supports are connected to the connecting plate, and the other ends of the supports are connected to the circular support base of the position-limit spring assembly; the three threaded inserts are respectively disposed in the three screw holes of the circular support base; the three screws are assembled with the three threaded inserts respectively; the three position-limit bodies are disposed on the three screws respectively; the three position-limit springs are nested outside the three screws respectively; one ends of the springs contact the position-limit bodies disposed on the screws; and the other ends of the springs contact an internal wall of the circular support base;

the first hydraulic mechanism and the second hydraulic mechanism have the same structure, and each of the first hydraulic mechanism and the second hydraulic mechanism comprises: circular pistons and circular oil cylinders fitting with the circular pistons respectively;

the first central position-limit mechanism and the bottom loading base of the testing machine are assembled; the circular support base of the position-limit spring assembly in the first central position-limit mechanism contacts the bottom loading base of the testing machine; the lower connector is disposed in a center hole of the circular support base; one ends of the three screws of the position-limit spring assembly in the first central position-limit mechanism contact an external side of the lower connector respectively; the second central position-limit mechanism and the lower end cap are assembled; the circular support base of the position-limit spring assembly in the second central position-limit mechanism contacts an outer bottom wall of the first sample fixing groove of the lower end cap; the first connecting segment of the lower end cap is disposed in the center hole of the circular support base; one ends of the three screws of the position-limit spring assembly in the second central position-limit mechanism contact an external side of the first connecting segment of the lower end cap; the first hydraulic mechanism and the first central position-limit mechanism are assembled; the circular oil cylinders of the first hydraulic mechanism are connected to the connecting plate of the first central position-limit mechanism; one end of the first spiral spring is connected to the circular pistons of the first hydraulic mechanism, and the other end of the first spiral spring is connected to the connecting plate of the second central position-limit mechanism; the lower chain is disposed in a space enclosed by the first central position-limit mechanism, the first hydraulic mechanism, the first spiral spring, and the second central position-limit mechanism; and the third central position-limit mechanism and the upper end cap are assembled; the circular support base of the position-limit spring assembly in the third central position-limit mechanism contacts an outer bottom wall of the second sample fixing groove of the upper end cap; the second connecting segment of the upper end cap is disposed in the center hole of the circular support base; one ends of the three screws of the position-limit spring assembly in the third central position-limit mechanism respectively contact an external side of the second connecting segment of the upper end cap; the fourth central position-limit mechanism and the top loading base of the testing machine are assembled; the circular support base of the position-limit spring assembly in the fourth central position-limit mechanism contacts the top loading base of the testing machine; the upper connector is disposed in the center hole of the circular support; one ends of the three screws of the position-limit spring assembly in the fourth central position-limit mechanism respectively contact an outer side of the upper connector; the second hydraulic mechanism and the third central position-limit mechanism are assembled; the circular oil cylinders of the second hydraulic mechanism are connected to the connecting plate of the third central position-limit mechanism; one end of the second spiral spring is connected to the circular pistons of the second hydraulic mechanism, and the other end of the second spiral spring is connected to the connecting plate of the fourth central position-limit mechanism; the upper chain is disposed in a space enclosed by the third central position-limit mechanism, the second hydraulic mechanism, the second spiral spring, and the fourth central position-limit mechanism.

2. The device of claim 1, wherein in the first central position-limit mechanism, the second central position-limit mechanism, the third central position-limit mechanism, and the fourth central position-limit mechanism, the supports are four round rods; the connecting plate is a circular plate; the four round rods are uniformly mounted between the circular support base and a circular surface of the connecting plate.

3. The device of claim 1, wherein in the first central position-limit mechanism, the second central position-limit mechanism, the third central position-limit mechanism, and the fourth central position-limit mechanism, the supports are two boards having a circular-arc cross section; the connecting plate is a circular plate; the two boards are symmetrically mounted between the circular support base and a circular surface of the connecting plate.

* * * * *